(12) United States Patent
Herzinger

(10) Patent No.: US 7,193,708 B1
(45) Date of Patent: Mar. 20, 2007

(54) TIME EFFICIENT METHOD FOR INVESTIGATING SAMPLE SYSTEMS WITH SPECTROSCOPIC ELECTROMAGNETIC RADIATION

(75) Inventor: Craig M. Herzinger, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 600 days.

(21) Appl. No.: 10/684,087

(22) Filed: Oct. 12, 2003

Related U.S. Application Data

(63) Continuation-in-part of application No. 10/376,677, filed on Feb. 28, 2003, now Pat. No. 6,982,792, and a continuation-in-part of application No. 09/531,877, filed on Mar. 21, 2000, now Pat. No. 6,535,286, said application No. 10/376,677 is a continuation-in-part of application No. 10/178,723, filed on Jun. 24, 2002, now Pat. No. 6,950,182, and a continuation-in-part of application No. 09/864,840, filed on May 24, 2001, now Pat. No. 6,456,376, and a continuation-in-part of application No. 09/845,548, filed on Apr. 30, 2001, now Pat. No. 6,585,128.

(60) Provisional application No. 60/427,043, filed on Nov. 18, 2002, provisional application No. 60/424,589, filed on Nov. 7, 2002, provisional application No. 60/300,714, filed on Jun. 26, 2001.

(51) Int. Cl.
*G01J 4/00* (2006.01)

(52) U.S. Cl. .................................................. 356/369
(58) Field of Classification Search ................ 356/369, 356/153, 399–402
See application file for complete search history.

(56) References Cited

U.S. PATENT DOCUMENTS

| | | | | |
|---|---|---|---|---|
| 4,311,393 | A * | 1/1982 | Bartke | 356/407 |
| 5,373,359 | A | 12/1994 | Woollam et al. | 356/328 |
| 5,666,201 | A | 9/1997 | Johs et al. | 356/369 |
| 5,700,961 | A * | 12/1997 | Anthony et al. | 73/866 |
| 5,822,063 | A * | 10/1998 | Suzuki et al. | 356/364 |
| 5,872,630 | A | 2/1999 | Johs et al. | 356/369 |
| 6,407,385 | B1 * | 6/2002 | Okada | 250/306 |
| 6,414,302 | B1 | 7/2002 | Freeouf | 250/225 |
| 6,628,397 | B1 * | 9/2003 | Nikoonahad et al. | 356/445 |
| 6,813,026 | B2 * | 11/2004 | McAninch | 356/445 |
| 2003/0071996 | A1 * | 4/2003 | Wang et al. | 356/369 |

* cited by examiner

*Primary Examiner*—Gregory J. Toetley, Jr.
*Assistant Examiner*—Isiaka O. Akanbi
(74) *Attorney, Agent, or Firm*—James D. Welch

(57) ABSTRACT

Time efficient methodology for investigating a sample system using electromagnetic wavelengths which are not absorbed by oxygen and/or water vapor during evacuation or purging of a substantially enclosed space in which is present the sample system, followed by using wavelengths which are absorbed by oxygen and/or water vapor after the evacuation or purging is sufficiently completed.

17 Claims, 6 Drawing Sheets

TIME EFFICIENT METHOD FOR INVESTIGATING SAMPLE SYSTEMS WITH SPECTROSCOPIC ELECTROMAGNETIC RADIATION

This application is a Continuation-In-Part of application Ser. No. 10/376,677 Filed Feb. 28, 2003 now U.S. Pat. No. 6,982,732, and is a CIP there via application Ser. No. 09/531,877 Filed Mar. 21, 2000 now U.S. Pat. No. 6,535,286; and said Ser. No. 10/376,677 is a CIP from Ser. No. 10/178,723 filed Jun. 24, 2002 now U.S. Pat. No. 6,950,182; and a CIP of Ser. No. 09/864,840 filed May 24, 2001 now U.S. Pat. No. 6,456,376; and a CIP of Ser. No. 09/845,548 filed Apr. 30, 2001 now U.S. Pat. No. 6,585,128; and Claims benefit of Provisional Application 60/300,714 filed Jun. 26, 2001; 60/424,589 Filed Nov. 7, 2002 and 60/427,043 Filed Nov. 18, 2002.

TECHNICAL FIELD

The disclosed invention relates to the use of electromagnetic radiation to monitor sample systems, and more particularly to methodology involving time efficient sequential obtaining of data using:
  wavelengths which are not absorbed by oxygen and water vapor during evacuation or purging of a substantially enclosed space in which is present a sample system, then
  wavelengths which are absorbed by oxygen and water vapor after said evacuation or purging is sufficiently completed.

BACKGROUND

Spectroscopic Ellipsometry (SE) was developed in the early 1970's after single wavelength ellipsometry had gained widespread acceptance. The first (SE) systems provided limited Ultraviolet (UV) to near Infrared (IR) spectral range capability, and with the exception of a few research instruments, this remained the case until the 1990's. Many challenges faced development of Vacuum Ultraviolet (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen or argon is utilized in place of vacuum at wavelengths which typically have an energy less than about 10 ev. The reason (VUV) ellipsometry must be carried out in vacuum or purging gas is that (VUV) wavelengths, are absorbed by oxygen and water vapor.

In the mid-1980's a Spectroscopic ellipsometer was constructed at the BESSY Synchrotron in Berlin for application in the (VUV) wavelength range, (eg. 5–35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J.A. Woollam Co. Inc. At present there are approximately twenty-five (25) Vacuum Ultraviolet Systems in use worldwide. It is noted that commercial (VUV) instruments, which provided wavelengths down to 146 nm, were introduced in response to the need for means to investigate material properties at 156 nm, which is utilized in lithography as applied to semiconductor gate oxide production.

A known patent which provides for use of VUV wavelength electromagnetic radiation through 10 eV is U.S. Pat. No. 6,414,302 B1 to Freeouf.

Continuing, it is important to appreciate that a typical ellipsometer system comprises:
  a. a source of a beam electromagnetic radiation;
  b. a polarizer element;
  c. optionally a compensator element;
  d. optional additional element(s);
  e. a stage for supporting a sample system;
  f. optional additional element(s);
  g. optionally a compensator element;
  h. an analyzer element; and
  i. a detector system.

Spectrophotometer systems delete the polarizer, analyzer and compensators, and the detector system can comprise either a single detector element or a plurality of detector elements. It is also noted that the combination of the source of a beam electromagnetic radiation and the polarizer element and the optional compensator element is often referred to as the Polarization State Generator, while the combination of the optional compensator element analyzer element and detector system is often referred to as the Polarization State Detector.

The practice of ellipsometry, polarimetry, spectrophotometry, reflectometry, scatterometry and the like, using Visible, Infrared (IR), (eg. 2–33 micron), and Ultraviolet (UV), (eg. 135–1700 nm), Electromagnetic Radiation Wavelengths, then is, as disclosed above, known. As mentioned, electromagnetic Radiation with wavelengths below about 190 nm is absorbed by atmospheric components such as Oxygen and Water Vapor. Thus, practice of Ellipsometry etc. using UV Wavelengths is typically carried out in vacuum or an atmosphere which does not contain oxygen and/or water vapor or other absorbing components. The J.A. Woollam Co. VUV-VASE, (Registered Trademark), for instance, utilizes a substantially enclosed Chamber which encompasses a substantially enclosed space which during use is purged by Nitrogen and/or Argon or functionally equivalent gas. (Note Nitrogen does not significantly absorb UV Range wavelengths, and Argon is in some respects even a better choice). It is noted that the J.A. Woollam Co. VUV-VASE has proven to provide good data in cases even when operated without Nitrogen or Argon purging, and has been applied to obtain reflection data using an electromagnetic beam caused to approach a sample system at a normal or oblique angle of incidence, transmission data with an electromagnetic beam being caused to approach a sample system at a normal or oblique angle of incidence, either using unpolarized electromagnetic radiation, partially polarized electromagnetic radiation or polarized electromagnetic radiation. That is very good data has been obtained utilizing unpolarized; partially polarized, randomly polarized; linearly polarized; with respect to a sample system linearly "p" polarized; with respect to a sample system linearly "s" polarized; and circularly polarized electromagnetic radiation in purged and atmospheric ambients.

The source of the electromagnetic radiation in the J.A. Woollam CO. VUV-VASE is preferably a Deuterium Lamp and/or a Xenon Lamp, which produce wavelengths of 115–400 nm, (of which 135–190 nm is used), and up to about 2000 nm, respectively. Specific wavelengths are selected by a J.A. Woollam Co. Monochromator which is a Cherny-Turner type Spectrometer sequentially comprising, mounted inside an enclosing means;
  a) source means for providing of a beam including ultraviolet wavelength range electromagnetic radiation;

b) a first slit;
c) a first spherical mirror;
d) a first stage comprising a plurality of gratings, each of which can be rotated into a functional position;
e) a second spherical mirror;
f) a second slit;
g) a third spherical mirror
h) a second stage comprising a plurality of gratings, each of which can be rotated into a functional position;
i) a forth spherical mirror; and
i) a pin hole;

there further being a beam chopper means present after said source means and typically just before said pin hole.

In use an electromagnetic beam from said source of the electromagnetic radiation is:
  caused to pass through said first slit;
  reflect from said first spherical mirror;
  interact with one of said plurality of gratings on said first stage which is rotated into a functional position;
  reflect from said second spherical mirror;
  pass through said second slit;
  reflect from said third spherical mirror;
  interact with one of said plurality of gratings on said second stage which is rotated into a functional position;
  reflect from said forth spherical mirror; and
  exit through said pinhole;

and at some point in said progression be subjected to chopping.

The gratings on said first and second stages are rotated into precise desired functional positions via stepper motors, separately controlled by computer. This has proven to provide superior precision and repeatability than commercially available grating positioning systems. Further, an electromagnetic radiation beam produced by said Monochromator has been shown to provide a highly collimated beam, with typical defining parameters being a 5 mm diameter at the pinhole output of the Monochromator, with divergence to about 20 mm diameter at 20 Feet, (ie. 6000 mm). This represents a divergence angle of only about 0.00125 radians, (ie. 0.07 Degrees).

In use, the monochromator system is utilized to provide a sequence of substantially single wavelengths which are applied to a sample system at least one angle of incidence, and while typically can be present anywhere between the source of a beam electromagnetic radiation and the detector in an ellipsometer system, is in the standard J.A. Woollam Co. VUV-VASE, for example, positioned directly after the source of a beam electromagnetic radiation.

It must be also appreciated that an alternative approach to obtaining data using monochromator systems, which apply only a substantially single wavelength at a time to a sample system, is to apply a multiplicity of wavelengths simultaneously and obtain data from each thereof simultaneously, but again, where the wavelength range includes wavelengths which are absorbed by oxygen and/or water vapor, the system must be placed into a substantially enclosed space into which is flowed purging gas. The J.A. Woollam Co. M2000, (Registered Trademark), is a relevant example of a Rotating Compensator Ellipsometer System, as described in U.S. Pat. No. 5,872,630 is incorporated herein by reference. Said 630 patent is a CIP from U.S. Pat. No. 5,666,201, which describes applying dispersing means to present numerous wavelengths to different detector elements simultaneously, in not only Rotating Compensator, but also Rotating Analyzer and Rotating Polarizer Ellipsometer Systems. Said 201 patent is further incorporated by reference hereinto. The 630 patent discloses a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensators) positioned at a location selected from the group consisting of:
  before said stage (STG) for supporting a material system (MS);
  after said stage (STG) for supporting a material system (MS); and
  both before and after said stage (STG) for supporting a material system (MS).

When said spectroscopic rotating compensator material system investigation system is used to investigate a material system present on said stage for supporting a material system, said analyzer and polarizer are maintained essentially fixed in position and at least one of said at least one compensators) is caused to continuously rotate while a polychromatic beam of electromagnetic radiation produced by said source of a polychromatic beam of electromagnetic radiation is caused to pass through said polarizer and at least one of said compensator(s). Said polychromatic beam of electromagnetic radiation is also caused to interact with said material system, pass through said analyzer and interact with said dispersive optics such that a multiplicity of essentially single wavelengths are caused to simultaneously enter a corresponding multiplicity of detector elements (DE's) in said at least one detector system.

The J.A. Woollam Co. Rotating Analyzer VASE (Registered Trademark), system, as described in U.S. Pat. No. 5,373,359, provides another example of such a system. Here-to-fore the J.A. Woollam CO. systems which utilize multiple detector element detectors have not been applied in purged substantially enclosed spaces.

It is noted that an ellipsometer or polarimeter system of the disclosed invention can involve selecting at least one detector system from the group consisting of:
  photo-diode;
  photo-diode array;
  charge-coupled-device;
  photo-multiplier tubes;
  photo-resistive elements;
  photo-conductive elements;
  thermo-piles;
  bolemeters; and
  having detector system distinguishing aperturing present.

Of particular importance to the disclosed invention is that inconveniences have been identified with, for instance, application of the described J.A. Woollam Co. VUV-VASE monochromator system in that outgassing of UV wavelength absorbing materials from such as wiring and electronic components etc., (purging of which is required), can require annoying periods of time. This problem is somewhat overcome by providing the J.A. Woollam Co. VUV-VASE a two-speed purge control means such that a sequestered subspace can be purged quickly and then sustained at a slower speed once purging is substantially complete, a Nitrogen conserving slower maintenance purge speed can be effected. And new monochromator design presently being developed, which provides less outgassing components therewithin, also promises to reduce purging time. A time delay, however, still exists between the beginning of purging and sufficient completion thereof, during which data can not be obtained using wavelengths which are absorbed by oxygen and water vapor, and this slows down data acquisition. Regardless of the ellipsometer system involved, while such a time delay can be minimized, it can never be eliminated. The disclosed invention provides methodology for optimizing use of time during data procurement wherein wavelengths applied to a sample system include those absorbed by oxygen and/or water vapor and wavelengths which are not so absorbed, comprising obtaining data using the later wavelengths during evacuation or purging.

In view of the state of the art, there remains need for methodology which can be practiced with either Monochromator or Dispersion based Polychromatic Ellipsometer, Polarimeter, Reflectometer, Spectrophotometer and the like systems which operate in a controlled ambient atmosphere inside a substantially Enclosed Space containing Chamber, (eg. to enable elimination of Oxygen and Water Vapor), using wavelengths both in and outside ranges in which said wavelengths are absorbed and not absorbed by oxygen and/or water vapor. The disclosed invention provides methodology for optimizing use of time during data procurement wherein wavelengths utilized include those absorbed by oxygen and/or water vapor and wavelengths which are not so absorbed.

DISCLOSURE OF THE INVENTION

In general, it should be appreciated that ellipsometer and polarimeter systems can be configured for use in both reflection and transmission modes and can comprise a source of monochromatic or polychromatic electromagnetic radiation. Via polarization state modifier means, typically a Polarizer and optional Compensator, a polarized beam of electromagnetic radiation is provided which is directed to interact with a material system placed on a stage. The combined Source and Polarization State Modifier is typically termed a Polarization State Generator. After interaction with a material system, a propagated electromagnetic beam passes through a polarization state analyzer and optional compensator, and enters a Detector System. The combined polarization state Analyzer and Detector System is typically termed a Polarization State Detector system. Where polarization state setting polarizer and optional compensator and analyzer and optional compensator are absent the resulting system can be termed a reflectometer or spectrophotometer system.

Vacuum Ultraviolet Ellipsometer System

A specific example of an ellipsometer or polarimeter system for analyzing sample systems using electromagnetic radiation with wavelengths in wavelength ranges which are absorbed by and not absorbed by oxygen and/or water vapor can be described as comprising a chamber means which encompasses a substantially enclosed space, functionally within said substantially enclosed space there being present:

a) source means for providing of a beam including ultraviolet wavelength range electromagnetic radiation;

b) polarization state setting means for setting a polarization state in at least a selected small range of wavelengths in a beam including ultraviolet wavelength range electromagnetic radiation;

c) a means for placing and maintaining a sample system in a desired position and orientation, said means for placing and maintaining a sample system in a desired position and orientation typically being positioned in a subspace of said substantially enclosed space which can be sequestered by a subspace sequestering means;

d) detector means for receiving an electromagnetic beam which is caused to interact with a sample system which is secured in place by said means for placing and maintaining a sample system in a desired position and orientation; and e) computer means for analyzing data provided by said detector means for receiving an electromagnetic beam after it interacts with said sample system; and f) means, such as a monochromator, for selecting a small range of wavelengths in a beam including ultraviolet wavelength range electromagnetic radiation which is present between said source means for providing of a beam including ultraviolet wavelength range electromagnetic radiation and said detector means for receiving an electromagnetic beam which is caused to interact with a sample system.

Said chamber means has functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation.

Said chamber further has means having functionally affixed thereto means for entering purging gas into said substantially enclosed space generally, and to a subspace sequestered by said subspace sequestering means independently when it is caused to be sequestered from said substantially enclosed space.

In use a sample system is caused to be affixed to said means for placing and maintaining a sample system in a desired position and orientation via said means for accessing said means for placing and maintaining a sample system in a desired position and orientation, and purging gas is caused to be entered into said substantially enclosed space via said means for entering purging gas into said substantially enclosed space generally, and/or to a subspace sequestered by said subspace sequestering means independently when it is caused to be sequestered from said substantially enclosed space. Further, said source means for providing of a beam including ultraviolet wavelength range electromagnetic radiation is caused to provide a beam including ultraviolet wavelength, and said polarization state setting means for setting a polarization state in a selected small range of wavelengths in a beam including ultraviolet wavelength range electromagnetic radiation is caused to impose a polarization state thereupon and said beam of ultraviolet wavelength range electromagnetic radiation. The result is that said means for placing and maintaining a sample system in a desired position and orientation is caused to orient said sample system and said beam including ultraviolet wavelength range electromagnetic radiation impinges thereupon at a known angle of incidence, so that said beam including ultraviolet wavelength range electromagnetic radiation interacts with said sample system and then enters said detector.

Preferred source means for providing of a beam of ultraviolet wavelength range electromagnetic radiation is selected from the group consisting of:

a Xenon lamp; and a Deuterium lamp.

Another specific example of an ellipsometer system for analyzing sample systems using electromagnetic radiation with wavelengths in wavelength ranges which are absorbed by and not absorbed by oxygen and/or water vapor can be described as comprising a chamber means which encompasses a substantially enclosed space, functionally within said substantially enclosed space there being present:

a) a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage (STG) for supporting a material system (MS);
after said stage (STG) for supporting a material system (MS); and
both before and after said stage (STG) for supporting a material system (MS).

When said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and at least one of said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements (DE's) in said at least one detector system.

Yet another specific example of an ellipsometer system for analyzing sample systems using electromagnetic radiation with wavelengths in wavelength ranges which are absorbed by and not absorbed by oxygen and/or water vapor can be described as comprising a chamber means which encompasses a substantially enclosed space, functionally within said substantially enclosed space there being present:

a) a spectroscopic rotating element material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating element material system investigation system further optionally comprising at least one compensator positioned at a location selected from the group consisting of:

before said stage for supporting a material system;
after said stage for supporting a material system; and
before and after said stage for supporting a material system.

When said spectroscopic rotating element material system investigation system is used to investigate a material system present on said stage for supporting a material system, at least one of said analyzer, polarizer or if present, compensator, is caused to continuously rotate while a polychromatic beam of electromagnetic radiation produced by said source of a polychromatic beam of electromagnetic radiation is caused to pass through said polarizer and, if present, said at least one compensator(s), said polychromatic beam of electromagnetic radiation being also caused to interact with said material system; said polychromatic beam of electromagnetic radiation being also, without further focusing, caused to pass through said analyzer and interact with said dispersive optics and enter at least one detector.

It is noted that said dispersive optics can provide a single spectrum of wavelengths to a single multi-detector element detector, or can serve to form a plurality of essentially spatially offset orders (+ORD2) (+ORD1) (−ORD1) (−ORD2) when said polychromatic beam of electromagnetic radiation (PPCLB) is caused to impinge thereupon, each said produced order (+ORD2) (+ORD1) (−ORD1) (−ORD2) comprising an essentially continuous spectrum of spatially separated electromagnetic beams of essentially single wavelengths, many of said essentially single wavelengths being present in two or more produced orders (+ORD2) (+ORD1) (−ORD1) (−ORD2). Where multiple orders are produces, first and second multiplicities of essentially single wavelength beams of electromagnetic radiation from first and second produced orders can be simultaneously intercepted by, respectively, first and second detector systems, thereby enabling the simultaneous accessing of a first multiplicity of essentially single wavelengths by said first detector system and a second multiplicity of essentially single wavelengths by said second detector system.

Methodology of Applying Vacuum Ultraviolet Ellipsometer System

Turning now to the focal point of the disclosed invention, a time efficient method of analyzing sample systems with spectroscopic electromagnetic radiation comprising wavelengths which are not absorbed by oxygen and/or water vapor and wavelengths which are absorbed by oxygen and/or water vapor, comprises the steps of:

In any functional order practicing steps a, a' and a":

a) providing a chamber which encloses a substantially enclosed space which contains oxygen and/or water vapor, to which chamber is functionally affixed a means for evacuating and/or purging said substantially enclosed space of oxygen and/or water vapor, and means for entering a beam of electromagnetic radiation thereinto, and a means for exiting electromagnetic radiation therefrom; and a') providing a source of a spectroscopic beam electromagnetic radiation comprising wavelengths which are not absorbed by oxygen and/or water vapor and wavelengths which are absorbed by oxygen and/or water vapor; and a") providing detector means of electromagnetic radiation;

and then proceeding to practice steps b and c:

b) positioning a sample system in said substantially enclosed space;

c) while causing said means for evacuating and/or purging said substantially enclosed space of oxygen and/or water vapor to evacuate or purge said substantially enclosed space of oxygen and/or water vapor, causing said source of a spectroscopic beam electromagnetic radiation to first comprise wavelengths which are not absorbed by oxygen and/or water vapor and sequentially later wavelengths which are absorbed by oxygen and/or water vapor and wavelengths and causing it to enter said means for entering a beam of electromagnetic radiation along a locus, such that it interacts with said sample system and exits said means for exiting electromagnetic radiation and enters said detector means of spectroscopic electromagnetic radiation.

During the evacuation or purging process, while oxygen and/or water vapor is still present in said substantially enclosed space in sufficient quantity to absorb said wavelengths which are absorbed by said oxygen and/or water vapor, data is provided by said detector means for wavelengths which are not absorbed by oxygen and/or water vapor, and such that once said substantially enclosed space is sufficiently evacuated or purged of oxygen and/or water vapor, data is provided by said detector for wavelengths which are absorbed by oxygen and/or water vapor.

A time efficient method of analyzing sample systems with spectroscopic electromagnetic radiation comprised both of wavelengths which are not absorbed by oxygen and/or water vapor and wavelengths which are absorbed by oxygen and/or water vapor, can also be recited as comprising the steps of:

a) providing an ellipsometer or polarimeter system, comprising, in a substantially enclosed space:
  a polarization state generation system comprising:
    source of electromagnetic radiation comprising wavelengths in ranges which are not absorbed and are absorbed by oxygen and/or water vapor; and
    polarization state setting means:
  means for placing and maintaining a sample system in a desired position and orientation;
  at least one polarization state detector system, each of which comprises:
    polarization state analyzer means: and
    detector system; and
  a computing means;

said substantially enclosed space comprising means for purging oxygen and water vapor therefrom;

such that, during use, a beam of electromagnetic radiation is produced by said source of electromagnetic radiation and caused to pass through said polarization state setting means, interact with a sample system placed on said means for placing and maintaining a sample system in a desired position and orientation, then pass through said polarization state analyzer means and enter a detector system in the pathway thereof;

b) positioning a sample system on said means for placing and maintaining a sample system in a desired position and orientation, and applying said means for purging oxygen and water vapor from said substantially enclosed space so that oxygen and water vapor are gradually replaced by at least one selection from the group consisting of:
  nitrogen and argon;

c) during said purging procedure obtaining data by monitoring wavelengths which are in the range which is not absorbed by oxygen and/or water vapor;

d) once purging is sufficiently complete obtaining data by monitoring wavelengths which are in the range which is absorbed by oxygen and/or water vapor;

e) in functional conjunction with the other steps proposing a mathematical model of the sample system;

f) applying said computing means to determine parameter values in said mathematical model which fit to said data obtained in both the wavelength range which is not and the wavelength range which is absorbed by oxygen and/or water vapor.

A time efficient method of analyzing a sample system using a beam of electromagnetic radiation with wavelengths in the ultraviolet wavelength range can further be recited as comprising the steps of:

A) providing an ellipsometer or polarimeter system for analyzing sample systems using electromagnetic radiation with wavelengths both in and out of the ultraviolet wavelength range, said ellipsometer or polarimeter system comprising a chamber means which encompasses a substantially enclosed space, functionally within said substantially enclosed space there being sequentially present:

a) source means for providing a beam of electromagnetic radiation including ultraviolet range wavelengths;

b) optional polarization state setting means for setting a polarization state in at least a selected small range of wavelengths in a beam of electromagnetic radiation including ultraviolet wavelengths;

c) optional means which enables sequentially modifying a polarization state set by said polarization state setting means, through a plurality of polarization states;

d) a means for placing and maintaining a sample system in a desired position and orientation, said means for placing and maintaining a sample system in a desired position and orientation being positioned in a subspace of said substantially enclosed space which subspace can be sequestered by a subspace sequestering means present within said substantially enclosed space;

e) detector means for receiving an electromagnetic beam which is caused to interact with a sample system which is secured in place by said means for placing and maintaining a sample system in a desired position and orientation; and f) computer means for analyzing data provided by said detector means for receiving an electromagnetic beam after it interacts with said sample system;

there being further present:

g) monochromator means, for selecting a small range of wavelengths in a beam including ultraviolet wavelength range electromagnetic radiation, present between said source means for providing of a beam including ultraviolet wavelength range electromagnetic radiation and said detector means for receiving an electromagnetic beam which is caused to interact with a sample system;

said chamber means having functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation;

said chamber further having means functionally affixed thereto for entering purging gas into said substantially enclosed space generally, and to a subspace sequestered by said subspace sequestering means independently when it is caused to be sequestered from said substantially enclosed space;

such that in use a sample system is caused to be affixed to said means for placing and maintaining a sample system in a desired position and orientation via said means for accessing said means for placing and maintaining a sample system in a desired position and orientation, and purging gas is caused to be entered into said substantially enclosed space via said means for entering purging gas into said substantially enclosed space generally, and/or to a subspace sequestered by said subspace sequestering means independently when it is caused to be sequestered from said substantially enclosed space, and said source means for providing of a beam including ultraviolet wavelength range electromagnetic radiation is caused to provide a beam including ultraviolet wavelength, and when present said polarization state setting means for setting a polarization state in a selected small range of wavelengths in a beam including ultraviolet wavelength range electromagnetic radiation is caused to impose a polarization state thereupon, and said monochromator means for selecting a small range of wavelengths in said beam of ultraviolet wavelength range electromagnetic radiation is caused to provide a small range of wavelengths in said beam of electromagnetic radiation which includes ultraviolet range wavelengths;

and such that said means for placing and maintaining a sample system in a desired position and orientation is caused to orient said sample system so that said beam including ultraviolet wavelength range electromagnetic radiation is caused to approach a surface thereof at a known angle of incidence;

and such that said beam including ultraviolet wavelength range electromagnetic radiation interacts with said sample system and then enters said detector;

B) via said means for causing said subspace sequestering means to become configured so as to sequester a sample system in a subspace of said substantially enclosed space, or to open and expose said sample system generally to the substantially enclosed space, entering a sample system to said subspace;

C) via said means for entering purging gas into said substantially enclosed space generally, and to a subspace sequestered by said subspace sequestering means independently when it is caused to be sequestered from said substantially enclosed space, purging said substantially enclosed space generally, and said subspace sequestered by said subspace sequestering means in particular until the subspace sequestered by said subspace sequestering means is sufficiently purged to be substantially free of oxygen and water vapor, followed by opening said subspace sequestered by said subspace sequestering means to the substantially enclosed space generally;

D) causing said means for placing and maintaining a sample system in a desired position and orientation, to rotate said sample system so that said beam of electromagnetic radiation of a known wavelength in the ultraviolet range approaches said surface of said sample system at a known angle-of-incidence thereto, and using said source means for providing of a beam of ultraviolet wavelength range electromagnetic radiation, and monochromator means for selecting a small range of wavelengths in a beam including ultraviolet wavelength range electromagnetic radiation, and said polarization state setting means for setting a polarization state in a selected small range of wavelengths in a beam including ultraviolet wavelength range electromagnetic radiation, sequentially providing a beam of electromagnetic radiation of a known wavelength beginning outside the ultraviolet range and progressing thereinto as purging progresses;

E) intercepting said beam of electromagnetic radiation of a known wavelength beginning outside the ultraviolet range, but which progresses thereinto as purging progresses, with said detector means for receiving an electromagnetic beam after it is caused to interact with said sample system;

F) in functional combination with the other steps proposing a parameter containing mathematical model for the sample system; and G) using said computer means for analyzing data provided by said detector means for receiving an electromagnetic beam after it interacts with said means for maintaining a sample system in a desired position and orientation, to simultaneously utilize data provided by said detector means in wavelength ranges both outside and in the ultraviolet range to evaluate parameters in said mathematical model.

The detector means can comprise, for instance, a selection from the group:
 at least two detectors, one sensitive outside the ultraviolet wavelength range and another sensitive in the ultraviolet wavelength range, and wherein said time efficient method further comprises sequentially first positioning said detector which is sensitive outside the ultraviolet wavelength range and then positioning said detector which is sensitive in the ultraviolet wavelength range to intercept said electromagnetic beam after it interacts with said sample system; or
 at least one detector which comprises a plurality of detector elements, in functional combinations with dispersive means for directing different wavelengths into different of said detector elements.

Where the system provided utilized allows, any of said methods of analyzing a sample system using a beam of electromagnetic radiation with wavelengths in the ultraviolet wavelength can be applied to a sample system characterized by a selection from the group consisting of:
 isotropic and non-depolarizing, (characterized by a Jones Matrix);
 isotropic and depolarizing;
 anisotropic and non-depolarizing;
 anisotropic and depolarizing, (thereby requiring a full Mueller Matrix characterization);

in which the beam of electromagnetic radiation provided by said source means for providing of a beam including ultraviolet wavelength range electromagnetic radiation, is characterized by a selection from the group consisting of:
 it comprises at least one wavelength;
 it comprises multiple wavelengths;
 it comprises a plurality of scanned wavelengths which are sequentially scanned individually;

and in which the beam of electromagnetic radiation is, just prior to said sample system characterized by a selection from the group consisting of:
 unpolarized;
 partially polarized;
 randomly polarized;
 linearly polarized;
 with respect to said sample system linearly "p" polarized;
 with respect to said sample system linearly "s" polarized;
 circularly polarized;

and is caused to interact with a sample system via a selection from the group consisting of:
 by reflection;
 by transmission;
 by both reflection and transmission;

at one or more angles of incidence, (AOI's), with respect to a surface thereof selected from the group consisting of:
 normal;
 oblique;

while said detector means is utilized to detect resulting:
 reflected;
 transmitted;
 scattered electromagnetic radiation.

The a beam of electromagnetic radiation with wavelengths in the ultraviolet wavelength range in which the electromagnetic radiation which is applied to a sample system can further be characterized by being, before and monitored after said sample system, respectively:

non-polarized incident, with measurement of intensity out;

non-polarized incident, with measurement of polarized out;

polarized incident, with measurement of intensity out;

polarized incident, with measurement of polarized out.

Further, said method of analyzing a sample system using a beam of electromagnetic radiation with wavelengths in the ultraviolet wavelength range can have modulation applied thereto during data accumulation, said modulation being of at least one selection from the group consisting of:

Electromagnetic Beam Magnetic "B" Field;
Electromagnetic Beam Electric "E" Field;
Electromagnetic Beam Flux "$E^2$";
Ambient Environment Composition, (eg. liquid, gas);
Sample System Temperature, (which can be above or below room temperature);
Sample System Strain;
Pressure applied to Sample System.

Said method of analyzing a sample system using a beam of electromagnetic radiation with wavelengths in, and out, of the ultraviolet wavelength can also involve providing polarizer means and accumulating ellipsometric PSI data while ellipsometric DELTA is placed within a range near 90 degrees via adjustment of the angle-of-incidence of the beam of electromagnetic radiation with respect to the surface of said sample system.

The disclosed invention will be better understood by reference to the Detailed Description Section of this Specification, in coordination with the Drawings.

SUMMARY OF THE INVENTION

It is therefore a primary purpose and/or objective of the disclosed invention to teach time efficient methodology for investigating a sample system comprising the sequential obtaining of data using electromagnetic wavelengths which are not absorbed by oxygen and/or water vapor during evacuation or purging of a substantially enclosed space in which is present a sample system, followed by using wavelengths which are absorbed by oxygen and/or water vapor after said evacuation or purging of the substantially enclosed space is sufficiently completed.

Other purposes and/or objectives of the disclosed invention will become apparent upon a reading of the Specification and Claims.

DETAILED DESCRIPTION

While the disclosed invention has as its primary focus methodology, it is of benefit to show non-limiting demonstrative systems for the practice thereof.

Figure 1:
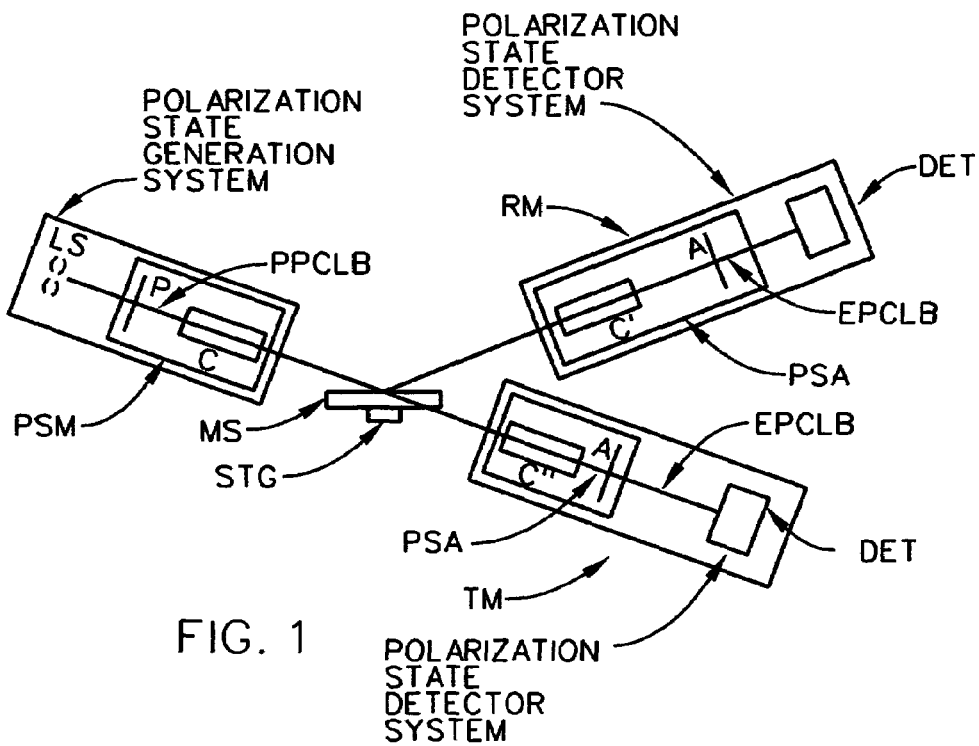
FIG. 1 shows a generalized diagram of an ellipsometer system with both reflection and transmission detectors.

FIG. 1 shows a demonstrative diagram of an ellipsometer/polarimeter system for use in both reflection (RF) and transmission (TM) modes. A source of polychromatic electromagnetic radiation (LS) is shown to, via polarization state modifier (PSM), which is demonstrated as being comprised of an Polarizer (P) and optionally a Compensator (C), provide a polarized beam of electromagnetic radiation (PPCLB) which is directed to interact with a material system (MS) which is placed on a stage (STG). (Note that conventional terminology identifies a Source System as a combination of said source of monochromatic or polychromatic electromagnetic radiation (LS) and a Polarization State Modifier (PSM), which Polarization State Modifier (PSM) is demonstrated as being comprised of a Polarizer (P) and optionally a Compensator (C)). After interaction with the material system (MS), propagated electromagnetic beam (PPCLB) emerges as (EPCLB), passes through a polarization state analyzer (PSA) and enters a detector system (DET). (Note that conventional terminology provides that for each of the Reflection (RM) and Transmission (TM) Modes, a Polarization State Analyzer (PSA) is demonstrated as being comprised of an Analyzer (A) and optionally a Compensator (C') or (C") respectively, and that when said Polarization State Analyzer (PSA) is combined with a Detector System (DET), there is formed a Reflection or Transmission Mode Polarization State Detector System, respectively). It is also to be understood that if the Polarization State Modifier (PSM), and Polarization State Analyzer (PSA) are not present, then FIG. 1 demonstrates a Reflectometer or Spectrophotometer system comprised of (LS), (STG/(MS) and (DET). It is to be understood that the angle of incidence of the electromagnetic beam (PPCLB) is often oriented closer to normal to the material sample (MS) upper surface, when the system is operated as a Reflectometer or Spectrophotometer.

Figure 2:
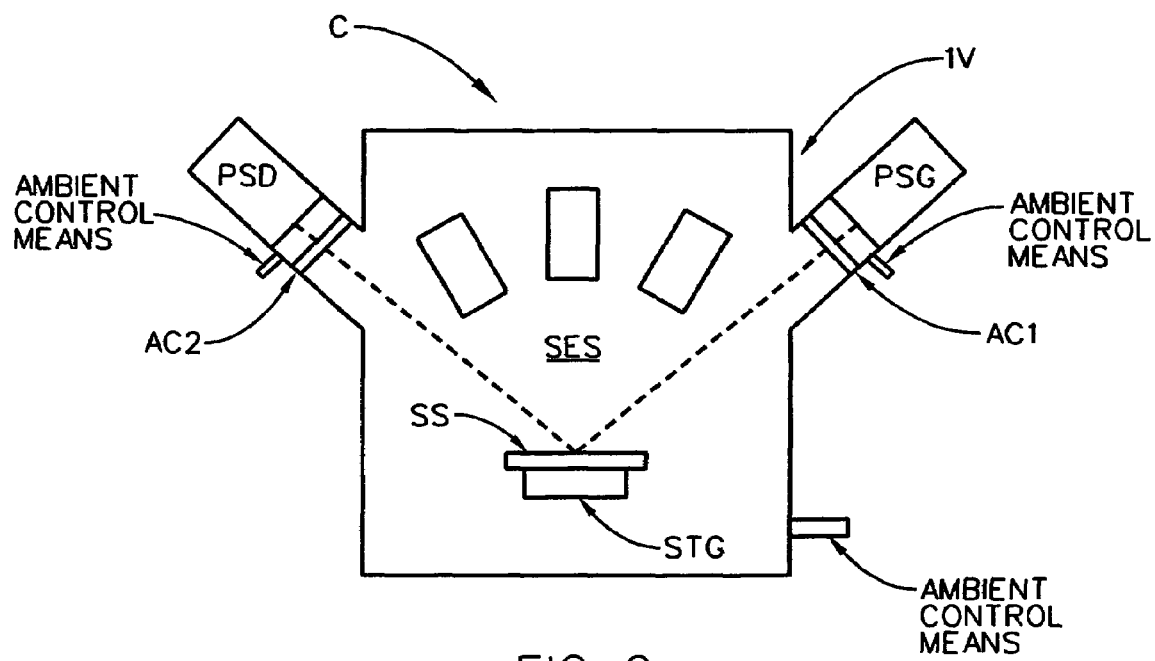
FIG. 2 shows a functional representation of a Chamber (CH) which contains a substantially enclosed space (SES).

FIG. 2 shows a functional representation of a Chamber (CH) which contains a substantially enclosed space (SES), Said Chamber (CH) can be of single section or multiple section substantially enclosed space (SES) construction. FIG. 2 is representative of Chamber means (CM) which functions to control the atmospheric content in a substantially enclosed space (SEC) in which is present a stage (STG) which in use supports a sample system. Any functional Chamber means (CM) are equivalent for the purposes of the disclosed invention.

Figure 3A:
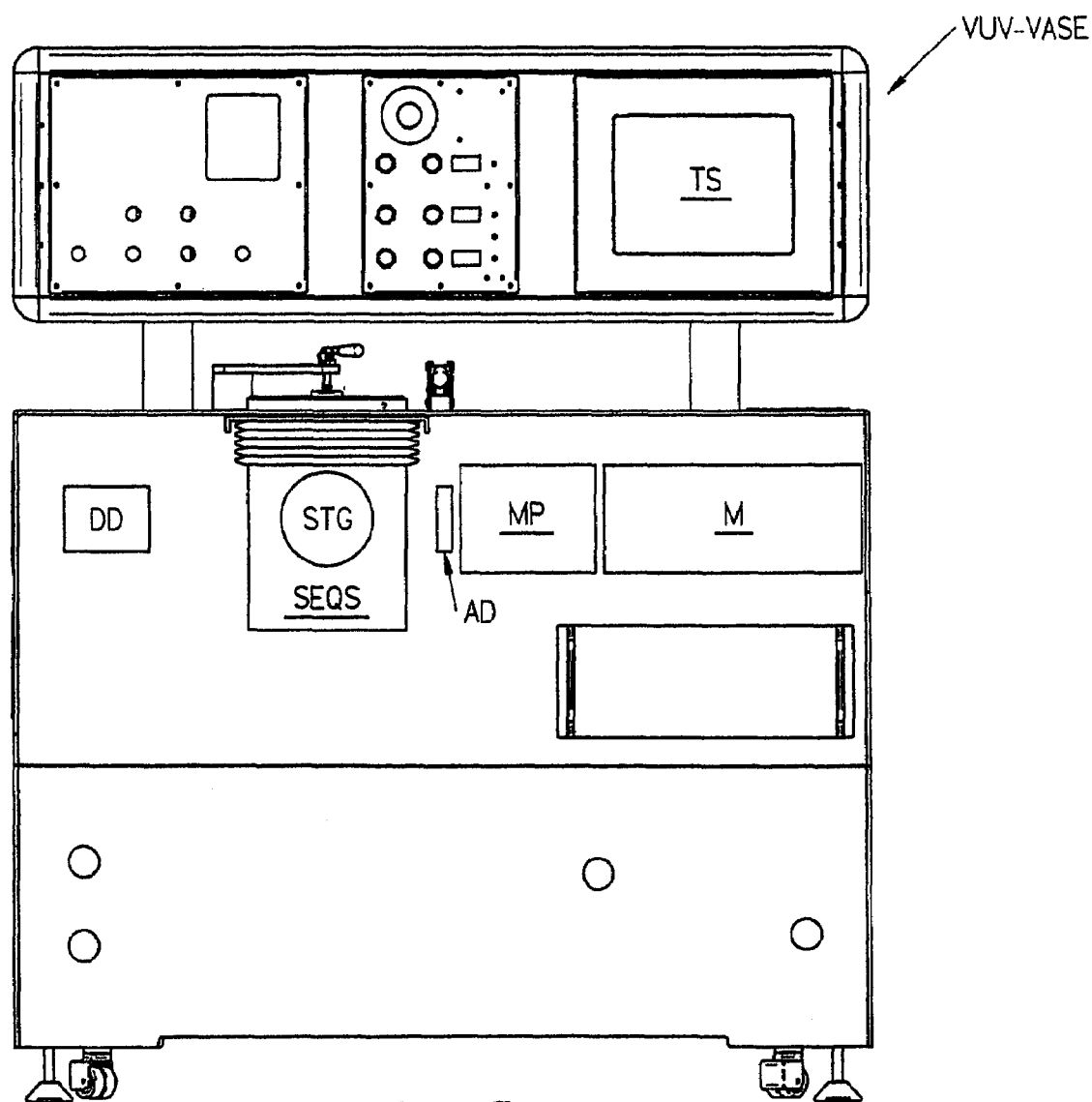
FIG. 3a provides a front elevational view showing the general layout of the J.A. Woollam Co. VUV-VASE.

FIG. 3a provides a front elevational view showing the general layout of the J.A. Woollam Co. VUV-VASE. Shown are a Monochromator (M), a Polarizer (MP), an Alignment Detector (AD) a Stage (STG) for supporting and aligning a sample system, said Stage (STG) being in a Sequestered Subspace (SEQS), a Data Detector (DD), and a Touch Screen (TS) Control Panel.

Figure 3B:
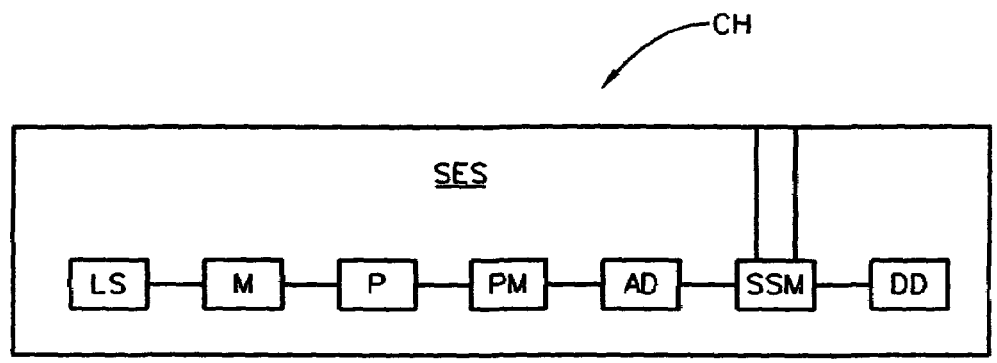
FIG. 3b shows a chamber (CH) which contains a substantially enclosed space (SES), with functional blocks corresponding to the J.A. Woollam CO. VUV-VASE components therewithin.

FIG. 3b shows a chamber (CH) which contains a substantially enclosed space (SES), with functional blocks corresponding to the J.A. Woollam CO. VUV-VASE components therewithin. Shown are a Source of electromagnetic radiation (LS), a Monochromator (M), a Polarizer (P), an Alignment Detector (AD), a Subspace Sequestering means (SSM) and a Data Detector (DD).

Figure 3C:
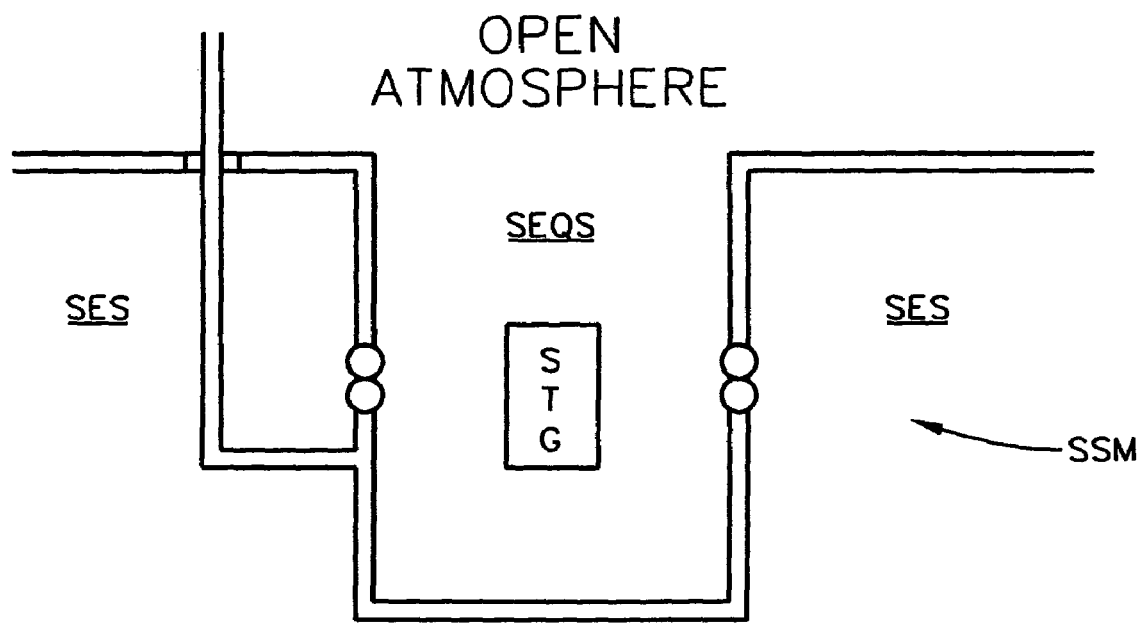
FIG. 3c shows a means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM), as identified in FIG. 3a via solid, (see FIG. 3c), and dashed, (see FIG. 3d), lines.

FIG. 3c shows a means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM), as identified in FIG. 3a.

Figure 3D:
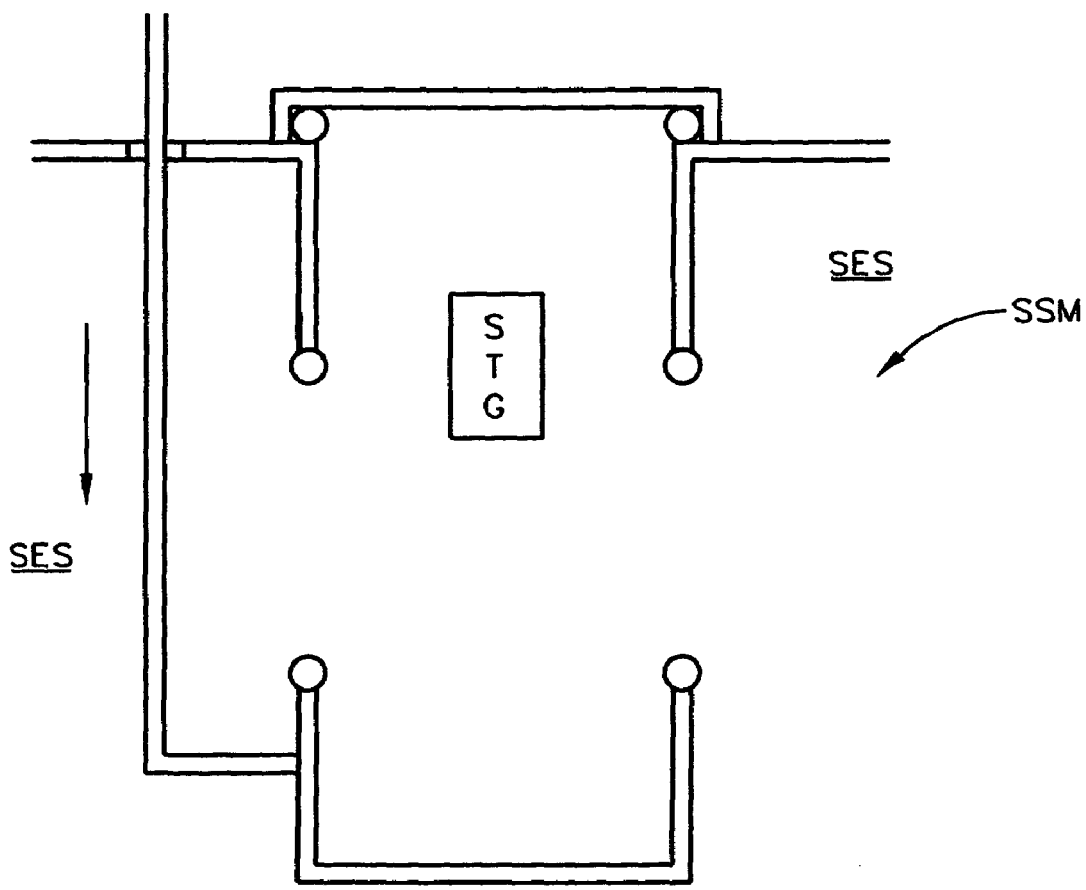
FIG. 3d shows the subspace sequestering means (SSM) identified in FIGS. 3a and 3b open to the substantially enclosed space (SES).

FIG. 3d shows the subspace sequestering means (SSM) identified in FIGS. 3a and 3b open to provide the sequestered subspace (SEQS) access to the substantially enclosed space (SES).

Figure 3E:
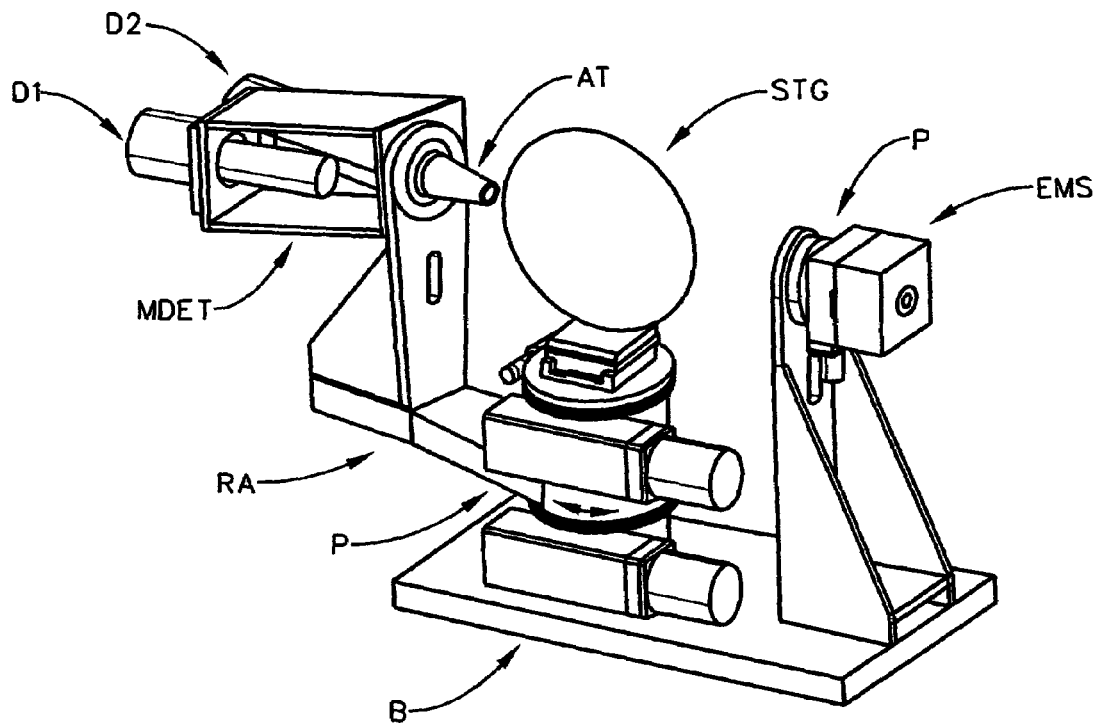
FIGS. 3e and 3f show multiple detector systems (MDET) comprised of at least detectors (D1) and (D2) which can be moved into the path of an electromagnetic beam via mechanical motion.
Figure 3F:
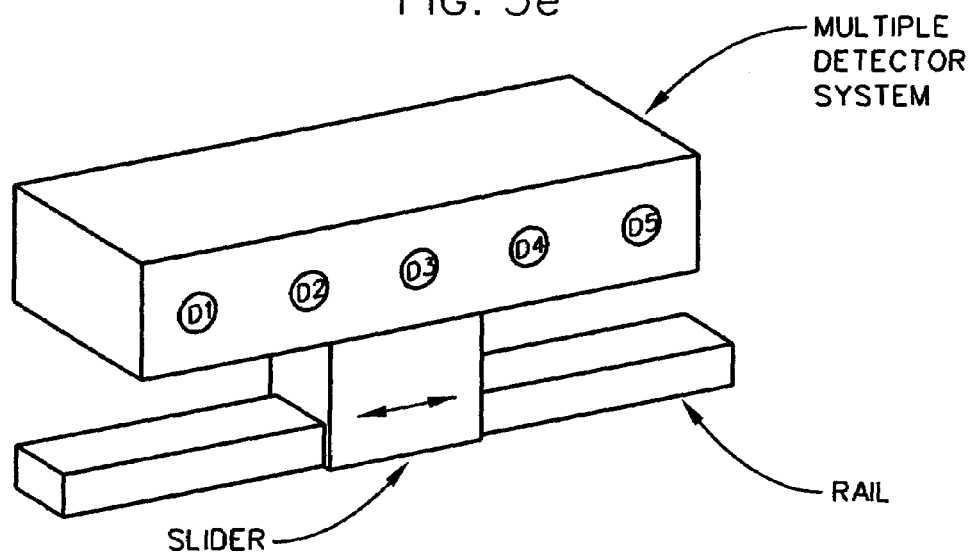

FIGS. 3e and 3f show multiple detector systems (MDET) comprised of at least detectors (D1) and (D2) which can be moved FIG. 3e shows a common base (B), to which are mounted a source of electromagnetic radiation (EMS) and a polarizer (P), a stage (STG) for supporting a material system in use, and a multiple detector system (MDET) which is comprised of two detector systems, (eg. first (D1) and second (D2) detector systems). Typically, though not necessarily, one of the first (D1) and second (D2) detector systems will be appropriate for detecting ellipsometric signals, and one for detecting spectrophotometric signals. Note that both first (D1) and second (D2) detector systems are mounted to rotatable arm (RA), and that rotatable arm (RA) is rotatable about a pivot point (P). In use it is easy for a user to, directly or via an automation system, rotate either the first (D1) or second (D2) detector system into place, while performing, for instance, calibration or data acquisition, respectively. Note that the such a rotation is shown in a horizontally oriented plane, but could be oriented in a vertically oriented plane. Rotation in any plane is within the scope of the present invention. FIG. 3f shows an alternative means, (linear rail and slider), for providing a plurality of positionable detector systems. Of course in a present invention system, said FIG. 3f can be oriented so that the Multiple Detector System slides horizontally or vertically or in between, with respect to an external frame of reference. (Note that the Data Detector (DD) of FIG. 3b functionally corresponds to (MDET) (D1) or (D2) as regards data collection.

Figure 4B:
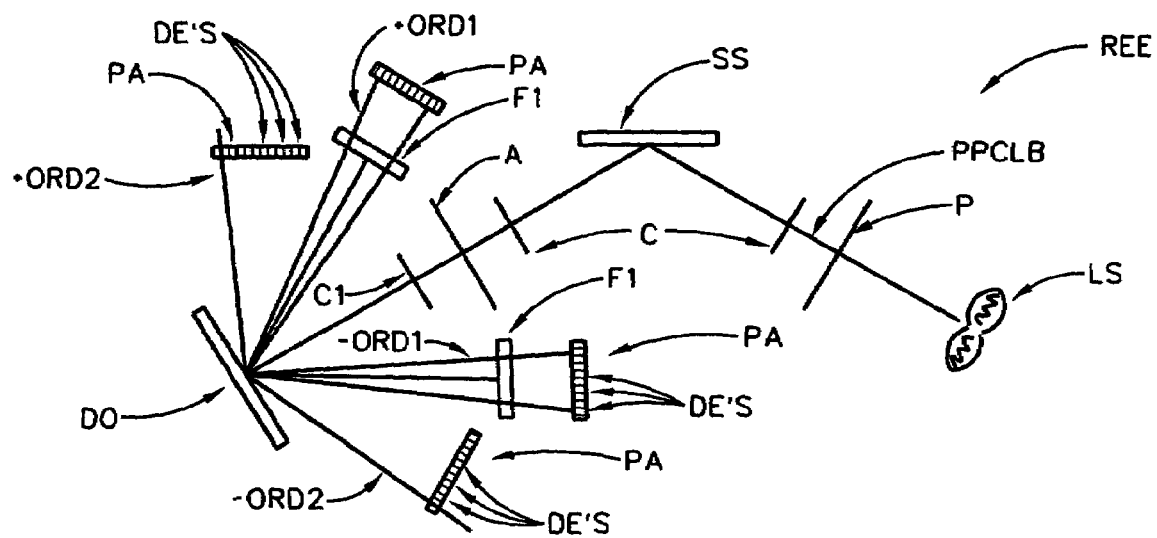
FIG. 4b shows detector system comprising a dispersion element and a plurality of detector elements.
Figure 4A:
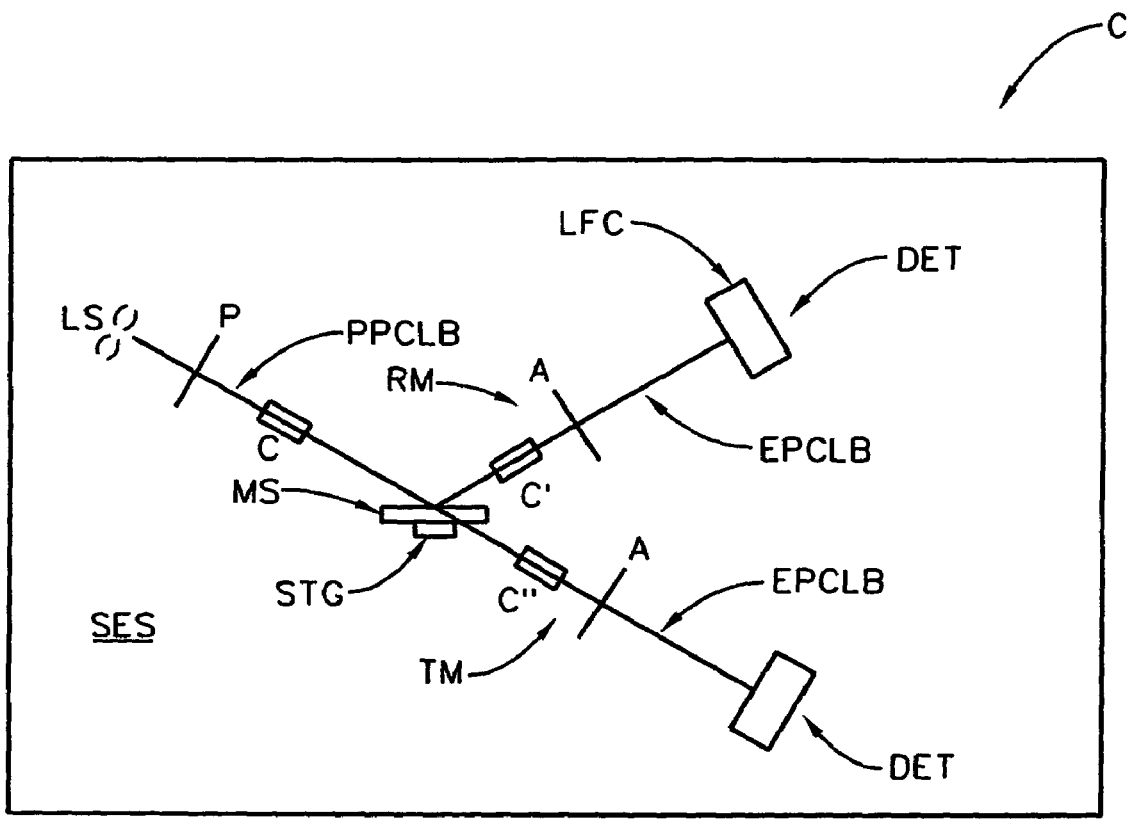
FIG. 4a shows a chamber (CH) which contains an essentially enclosed space (SES), with functional blocks corresponding to a J.A. Woollam CO. M-2000 components present therewithin.

FIG. 4a shows a chamber (CH) which contains an essentially enclosed space (SES), with functional blocks corresponding to a J.A. Woollam CO. M-2000 components present therewithin.

FIG. 4b shows detector system comprising a dispersive element (DO) and a plurality of detectors (PA), each comprising a plurality of detector elements (DE). The detectors (PA) are positioned to intercept various orders (+ORD2) (+ORD1), (−ORD1), (−ORD2) produced by said dispersive element (DO), It should be understood that only a single order wavelength spectrum intercepting detector might be present in a system for practicing the disclosed invention.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A time efficient method of analyzing sample systems with spectroscopic electromagnetic radiation comprising wavelengths which are not absorbed by oxygen and/or water vapor and wavelengths which are absorbed by oxygen and/or water vapor, comprising the steps of:

in any functional order practicing steps a, a' and a":

a) providing a chamber which encloses a substantially enclosed space which contains oxygen and/or water vapor, to which chamber is functionally affixed a means for evacuating and/or purging said substantially enclosed space of oxygen and/or water vapor, and means for entering a beam of electromagnetic radiation thereinto, and a means for exiting electromagnetic radiation therefrom; and a') providing a source of a spectroscopic beam electromagnetic radiation comprising wavelengths which are not absorbed by oxygen and/or water vapor and wavelengths which are absorbed by oxygen and/or water vapor; and a") providing detector means of electromagnetic radiation;

and then proceeding to practice steps b and c and d:

b) positioning a sample system in said substantially enclosed space;

c) while causing said means for evacuating and/or purging said substantially enclosed space of oxygen and/or water vapor to evacuate or purge said substantially enclosed space of oxygen and/or water vapor, causing said source of a spectroscopic beam electromagnetic radiation to first comprise wavelengths which are not absorbed by oxygen and/or water vapor and causing said beam to enter said means for entering a beam of electromagnetic radiation along a locus, such-that said beam interacts with said sample system and exits said means for exiting electromagnetic radiation and enters said detector means of electromagnetic radiation; and d) sequentially later after evacuation and/or purging is substantially complete, causing said source of a spectroscopic beam electromagnetic radiation to comprise wavelengths which are absorbed by oxygen and/or water vapor and causing said beam to enter said means for entering a beam of electromagnetic radiation along a locus, such that it interacts with said sample system and exits said means for exiting electromagnetic radiation and enters said detector means of electromagnetic radiation;

such that during the evacuation or purging process, while oxygen and/or water vapor is still present in said substantially enclosed space in sufficient quantity to absorb said wavelengths which are absorbed by said oxygen and/or water vapor, data is provided by said detector means for wavelengths which are not absorbed by oxygen and/or water vapor, and such that once said substantially enclosed space is sufficiently evacuated or purged of oxygen and/or water vapor, data is provided by said detector means for wavelengths which are absorbed by oxygen and/or water vapor.

2. A time efficient method as in claim 1, in which the sample system is characterized by a selection from the group consisting of:
- being isotropic and non-depolarizing;
- being isotropic and depolarizing;
- being anisotropic and non-depolarizing;
- being anisotropic and depolarizing;

and in which the beam of electromagnetic radiation provided by said source means for providing of a beam including ultraviolet wavelength range electromagnetic radiation which interacts with said sample system is characterized by a selection from the group consisting of:
- it simultaneously comprises multiple wavelengths;
- it comprises a plurality of scanned wavelengths which are sequentially scanned individually;

and in which the beam of electromagnetic radiation is, just prior to said sample system caused to be characterized by a selection from the group consisting of:
- unpolarized;
- partially polarized;
- randomly polarized;
- linearly polarized;
- with respect to said sample system linearly "p" polarized;
- with respect to said sample system linearly "s" polarized;
- circularly polarized;

and is caused to interact with a sample system via a selection from the group consisting of:
- by reflection;
- by transmission;
- by both reflection and transmission;

at one or more angles of incidence, (AOI's), with respect to a surface thereof selected from the group consisting of:
- normal;
- oblique;

while said detector means is utilized to detect resulting:
- reflected;
- transmitted;
- scattered electromagnetic radiation.

3. A time efficient method as in claim 1, in which the electromagnetic radiation which is applied to a sample system and monitored after said sample system, are each characterized by a selection from the group consisting of:
- non-polarized incident, with measurement of intensity out;
- non-polarized incident, with measurement of polarized out;
- polarized incident, with measurement of intensity out;
- polarized incident, with measurement of polarized out.

4. A time efficient method as in claim 1, in which modulation is applied during data accumulation, said modulation being of at least one selection from the group consisting of:
- Electromagnetic Beam Magnetic "B" Field;
- Electromagnetic Beam Electric "E" Field;
- Electromagnetic Beam Flux "$E^2$";
- Ambient Environment Composition, (eg. liquid, gas);
- Sample System Temperature, (which can be above or below room temperature);
- Sample System Strain;
- Pressure applied to Sample System.

5. A time efficient method as in claim 1, in which a polarizer means is present and in which ellipsometric PSI data is accumulated while ellipsometric DELTA is placed within a range near 90 degrees via adjustment of the angle-of-incidence of the beam of electromagnetic radiation with respect to the surface of said sample system.

6. A time efficient method as in claim 1, in which the step of providing a source of a spectroscopic beam includes providing a selection from the group consisting of:
- a monochromator which is utilized to sequentially select wavelengths which are individually provided to a detector means element after interaction with said sample system;
- a dispersive element is present which simultaneously provides a plurality of wavelengths to separate detector means elements after interaction with said sample system.

7. A time efficient method of analyzing sample systems with spectroscopic electromagnetic radiation comprised both of wavelengths which are not absorbed by oxygen and/or water vapor and wavelengths which are absorbed by oxygen and/or water vapor, comprising the steps of:
  a) providing an ellipsometer or polarimeter system, comprising, in a substantially enclosed space:
  a polarization state generation system comprising:
    source of electromagnetic radiation comprising wavelengths in ranges which are not absorbed and are absorbed by oxygen and/or water vapor; and
    polarization state setting means:
  means for placing and maintaining a sample system in a desired position and orientation;
  at least one polarization state detector system, each of which comprises:
    polarization state analyzer means: and
    detector system; and
  a computing means;
said substantially enclosed space comprising means for purging oxygen and water vapor therefrom;
such that, during use, a beam of electromagnetic radiation is produced by said source of electromagnetic radiation and caused to pass through said polarization state setting means, interact with a sample system placed on said means for placing and maintaining a sample system in a desired position and orientation, then pass through said polarization state analyzer means and enter a detector system in the pathway thereof;
  b) positioning a sample system on said means for placing and maintaining a sample system in a desired position and orientation, and applying said means for purging oxygen and water vapor from said substantially enclosed space so that oxygen and water vapor are gradually replaced by at least one selection from the group consisting of:
  nitrogen and argon;
  c) during said purging procedure obtaining data by monitoring wavelengths which are in the range which is not absorbed by oxygen and/or water vapor;
  d) once purging is sufficiently complete obtaining data by monitoring wavelengths which are in the range which is absorbed by oxygen and/or water vapor;
  e) in functional conjunction with the other steps proposing a parameter containing mathematical model of the sample system;
  f) applying said computing means to evaluate parameters in said mathematical model which fit to said data obtained in both the wavelength range which is not and the wavelength range which is absorbed by oxygen and/or water vapor.

8. A time efficient method as in claim 7, in which step of providing a an ellipsometer or polarimeter system, involves selecting at least one detector system from the group consisting of:
- photo-diode;
- photo-diode array;
- charge-coupled-device;
- photo-multiplier tubes;
- photo-resistive elements;
- photo-conductive elements;
- thermo-piles;
- bolemeters; and having detector system distinguishing aperturing present.

9. A time efficient method as in claim 7, in which step of providing a an ellipsometer system, involves selecting a detector system comprising a plurality of detector elements.

10. A time efficient method of analyzing a sample system using a beam of electromagnetic radiation with wavelengths in the ultraviolet wavelength range as in claim 7, in which the sample system is characterized by a selection from the group consisting of:
- being isotropic and non-depolarizing;
- being isotropic and depolarizing;
- being anisotropic and non-depolarizing;
- being anisotropic and depolarizing;

and in which the beam of electromagnetic radiation provided by said source means for providing of a beam including ultraviolet wavelength range electromagnetic radiation, is characterized by a selection from the group consisting of:
- it simultaneously comprises multiple wavelengths;
- it comprises a plurality of scanned wavelengths which are sequentially scanned individually;

and in which the beam of electromagnetic radiation is, just prior to said sample system characterized by a selection from the group consisting of:
- unpolarized;
- partially polarized;
- randomly polarized;
- linearly polarized;
- with respect to said sample system linearly "p" polarized;
- with respect to said sample system linearly "s" polarized;
- circularly polarized;

and is caused to interact with a sample system via a selection from the group consisting of:
- by reflection;
- by transmission;
- by both reflection and transmission;

at one or more angles of incidence, (AOI's), with respect to a surface thereof selected from the group consisting of:
- normal;
- oblique;

while said detector system is utilized to detect at least one selection from the group consisting of:
- reflected;
- transmitted; and
- scattered;

electromagnetic radiation.

11. A time efficient method as in claim 7, in which the electromagnetic radiation which is applied to a sample system and is characterized by being, provided before and monitored after said sample system, respectively:
- non-polarized incident, with measurement of intensity out;
- non-polarized incident, with measurement of polarized out;
- polarized incident, with measurement of intensity out;
- polarized incident, with measurement of polarized out.

12. A time efficient method as in claim 7, in which modulation is applied during data accumulation, said modulation being of at least one selection from the group consisting of:
- Electromagnetic Beam Magnetic "B" Field;
- Electromagnetic Beam Electric "E" Field;
- Electromagnetic Beam Flux "$E^2$";
- Ambient Environment Composition, (eg. liquid, gas);
- Sample System Temperature, (which can be above or below room temperature);
- Sample System Strain;
- Pressure applied to Sample System.

13. A time efficient method as in claim 7, in which ellipsometric PSI data is accumulated while ellipsometric DELTA is placed within a range near 90 degrees via adjustment of the angle-of-incidence of the beam of electromagnetic radiation with respect to the surface of said sample system.

14. A time efficient method as in claim 7, in which said polarization state setting means is sequentially set to at least two settings while data is obtained at each thereof.

15. A time efficient method of analyzing a sample system using a beam of electromagnetic radiation with wavelengths in the ultraviolet wavelength range comprising the steps of:
- A) providing an ellipsometer or polarimeter system for analyzing sample systems using electromagnetic radiation with wavelengths both in and out of the ultraviolet wavelength range, said ellipsometer or polarimeter system comprising a chamber means which encompasses a substantially enclosed space, functionally within said substantially enclosed space there being sequentially present:
  - a) source means for providing a beam of electromagnetic radiation including ultraviolet range wavelengths;
  - b) optional polarization state setting means for setting a polarization state in at least a selected small range of wavelengths in a beam of electromagnetic radiation including ultraviolet wavelengths;
  - c) optional means which enables sequentially modifying a polarization state set by said polarization state setting means, through a plurality of polarization states;
  - d) a means for placing and maintaining a sample system in a desired position and orientation, said means for placing and maintaining a sample system in a desired position and orientation being positioned in a subspace of said substantially enclosed space which subspace can be sequestered by a subspace sequestering means present within said substantially enclosed space;
  - e) detector means for receiving an electromagnetic beam which is caused to interact with a sample system which is secured in place by said means for placing and maintaining a sample system in a desired position and orientation; and
  - f) computer means for analyzing data provided by said detector means for receiving an electromagnetic beam after it interacts with said sample system;

there being further present:
- g) monochromator means, for selecting a small range of wavelengths in a beam including ultraviolet wavelength range electromagnetic radiation, present between said source means for providing of a beam including ultraviolet wavelength range electromagnetic radiation and said detector means for receiving an electromagnetic beam which is caused to interact with a sample system;

said chamber means having functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation;

said chamber further having means functionally affixed thereto for entering purging gas into said substantially enclosed space generally, and to a subspace sequestered by said subspace sequestering means independently when it is caused to be sequestered from said substantially enclosed space;

such that in use a sample system is caused to be affixed to said means for placing and maintaining a sample system in a desired position and orientation via said means for accessing said means for placing and maintaining a sample system in a desired position and orientation, and purging gas is caused to be entered into said substantially enclosed space via said means for entering purging gas into said substantially enclosed space generally, and/or to a subspace sequestered by said subspace sequestering means independently when it is caused to be sequestered from said substantially enclosed space, and said source means for providing of a beam including ultraviolet wavelength range electromagnetic radiation is caused to provide a beam including ultraviolet wavelength, and when present said polarization state setting means for setting a polarization state in a selected small range of wavelengths in a beam including ultraviolet wavelength range electromagnetic radiation is caused to impose a polarization state thereupon, and said monochromator means for selecting a small range of wavelengths in said beam of ultraviolet wavelength range electromagnetic radiation is caused to provide a small range of wavelengths in said beam of electromagnetic radiation which includes ultraviolet range wavelengths;

and such that said means for placing and maintaining a sample system in a desired position and orientation is caused to orient said sample system so that said beam including ultraviolet wavelength range electromagnetic radiation is caused to approach a surface thereof at a known angle of incidence;

and such that said beam including ultraviolet wavelength range electromagnetic radiation interacts with said sample system and then enters said detector;

B) via said means for causing said subspace sequestering means to become configured so as to sequester a sample system in a subspace of said substantially enclosed space, or to open and expose said sample system generally to the substantially enclosed space, entering a sample system to said subspace;

C) via said means for entering purging gas into said substantially enclosed space generally, and to a subspace sequestered by said subspace sequestering means independently when it is caused to be sequestered from said substantially enclosed space, purging said substantially enclosed space generally, and said subspace sequestered by said subspace sequestering means in particular until the subspace sequestered by said subspace sequestering means is sufficiently purged to be substantially free of oxygen and water vapor, followed by opening said subspace sequestered by said subspace sequestering means to the substantially enclosed space generally;

D) causing said means for placing and maintaining a sample system in a desired position and orientation, to rotate said sample system so that said beam of electromagnetic radiation of a known wavelength in the ultraviolet range approaches said surface of said sample system at a known angle-of-incidence thereto, and using said source means for providing of a beam of ultraviolet wavelength range electromagnetic radiation, and monochromator means for selecting a small range of wavelengths in a beam including ultraviolet wavelength range electromagnetic radiation, and said polarization state setting means for setting a polarization state in a selected small range of wavelengths in a beam including ultraviolet wavelength range electromagnetic radiation, sequentially providing a beam of electromagnetic radiation of a known wavelength beginning outside the ultraviolet range and progressing thereinto as purging progresses;

E) intercepting said beam of electromagnetic radiation of a known wavelength beginning outside the ultraviolet range, but which progresses thereinto as purging progresses, with said detector means for receiving an electromagnetic beam after it is caused to interact with said sample system;

F) in functional combination with the other steps proposing a parameter containing mathematical model for the sample system; and G) using said computer means for analyzing data provided by said detector means for receiving an electromagnetic beam after it interacts with said means for maintaining a sample system in a desired position and orientation, to simultaneously utilize data provided by said detector means in wavelength ranges both outside and in the ultraviolet range to evaluate parameters in said mathematical model.

16. A time efficient method as in claim 15, in which said detector means comprises at least two detectors, one sensitive outside the ultraviolet wavelength range and another sensitive in the ultraviolet wavelength range, and wherein said time efficient method further comprises sequentially first positioning said detector which is sensitive outside the ultraviolet wavelength range and then positioning said detector which is sensitive in the ultraviolet wavelength range to intercept said electromagnetic beam after it interacts with said sample system.

17. A time efficient method as in claim 15, in which said detector means comprises at least one detector which comprises a plurality of detector elements, in functional combination with dispersive means for directing different wavelengths into different of said detector elements.

\* \* \* \* \*